(12) United States Patent
Trovato

(10) Patent No.: US 8,535,336 B2
(45) Date of Patent: Sep. 17, 2013

(54) NESTED CANNULAE FOR MINIMALLY INVASIVE SURGERY

(75) Inventor: Karen Irene Trovato, Putnam Valley, NY (US)

(73) Assignee: Koninklijke Philips N.V., Eindhoven (NL)

( * ) Notice: Subject to any disclaimer, the term of this patent is extended or adjusted under 35 U.S.C. 154(b) by 239 days.

(21) Appl. No.: 12/991,913

(22) PCT Filed: Jun. 12, 2009

(86) PCT No.: PCT/IB2009/052521
§ 371 (c)(1),
(2), (4) Date: Nov. 10, 2010

(87) PCT Pub. No.: WO2009/156892
PCT Pub. Date: Dec. 30, 2009

(65) Prior Publication Data
US 2011/0092810 A1   Apr. 21, 2011

Related U.S. Application Data

(60) Provisional application No. 61/075,401, filed on Jun. 25, 2008.

(51) Int. Cl.
*A61B 19/00* (2006.01)

(52) U.S. Cl.
USPC .......................................... 606/130; 600/424

(58) Field of Classification Search
USPC ......... 600/424, 214; 606/130, 108; 604/116, 604/164
See application file for complete search history.

(56) References Cited

U.S. PATENT DOCUMENTS

| 5,054,867 A | 10/1991 | Wagnieres et al. |
| 5,454,794 A | 10/1995 | Narciso et al. |
| 5,788,713 A * | 8/1998 | Dubach et al. ................ 606/130 |
| 6,589,164 B1 | 7/2003 | Flaherty |
| 7,153,299 B1 | 12/2006 | Tu et al. |
| 2003/0159700 A1 | 8/2003 | Laufer et al. |

(Continued)

FOREIGN PATENT DOCUMENTS

| DE | 4223897 | 1/1994 |
| WO | WO2006058195 | 6/2006 |
| WO | WO2007059233 | 5/2007 |
| WO | WO2008032230 | 3/2008 |

OTHER PUBLICATIONS

Patrick Sears et al., "Inverse Kinematics of Concentric Tube Steerable Needles", 2007 IEEE International Conference on Robotics and Automation, Rome, Italy, Apr. 10-14, 2007, pp. 1887-1892.

*Primary Examiner* — Sanjay Cattungal

(57) ABSTRACT

The present disclosure provides for systems and methods for Nested Cannula configuration. Nested Cannula systems include a plurality of telescoping, pre-shaped tubes configured and dimensioned to reach target locations within a particular anatomical region. A three dimensional image is read for the particular anatomical region and structure in question. A series of arcs are generated between a point of the anatomical region and a target location, ensuring collision-free motion for each of the tubes at each specific diameter. The target location is determined based upon the medical procedure being performed and the location and orientation in six degrees of freedom of the anatomical structure in question. The series of arcs are used to configure and dimension the plurality of tubes. The Nested Cannula system is adapted to reach relatively small and complex target locations, such as to deliver photodynamic therapy, balloon angioplasty or BronchoAlveolar Lavage.

38 Claims, 8 Drawing Sheets

(56) References Cited

U.S. PATENT DOCUMENTS

| | | |
|---|---|---|
| 2005/0112131 A1 | 5/2005 | Pogue et al. |
| 2007/0020272 A1 | 1/2007 | Hasan |
| 2007/0288030 A1 | 12/2007 | Metzger et al. |
| 2009/0248045 A1* | 10/2009 | Trovato .................. 606/130 |
| 2010/0063496 A1* | 3/2010 | Trovato et al. ........... 606/34 |
| 2011/0201887 A1* | 8/2011 | Greenblatt et al. ....... 600/130 |

\* cited by examiner

NESTED CANNULAE FOR MINIMALLY INVASIVE SURGERY

Cross Reference to Related Cases

Applicant claims the benefit of International Application Number PCT/IB2009/052521, filed Jun. 12, 2009, and Provisional Application Ser. No. 61/075,401, filed Jun. 25, 2008.

The present disclosure generally relates to minimally invasive surgical and to other medical procedures. More particularly, the present disclosure relates to systems and methods related to nested cannula designs and configurations that are customized to a patient's particular anatomical composition to facilitate effective minimally invasive surgical procedures.

Existing navigation devices, such as catheters and bronchoscopes, have several disadvantages. A particular problem encountered in bronchoscope applications is that the bronchoscope typically has a relatively large tube diameter and can only turn or be otherwise navigated at the tip. The large size is partly due to the control mechanism built within the bronchoscope that enables it to turn. As a result of their size and lack of dexterity, conventional bronchoscopes are limited in their ability to reach certain regions. For example, a typical bronchoscope can only reach the center third of a lung, where the largest airways are located. This leaves two-thirds of all lung cancers (for example) unreachable with conventional bronchoscope technology and, therefore, untreatable without major physical intervention. Even a lung biopsy, which might distinguish a benign from malignant nodule, has up to a 40% chance of causing lung collapse. Thus, potentially treatable diseases are often left untreated until the disease is so aggressive that surgery is warranted and/or required.

Catheters and guidewires associated with traditional surgical techniques are relatively flexible and can reach deep within the body by following vessels. However, these devices have a tip shape designed to address the most difficult of the likely turns within the anatomy. A particular device's ability to maneuver through only one type of challenging turn limits the applicability of the device. Often, catheters and guidewires are used in an 'upstream' direction, where the vessel branching requires no specific control, saving the one difficult turn for a specific location. For example, insertion of a catheter into a distal artery, such as the femoral artery (used in balloon angioplasty), toward the heart means that vessels are joining in this direction, rather than dividing. While this is effective in many cases, there is no effective mechanism to traverse complex arteries as they travel with the blood as it flows away from the heart, or along veins leading away from the heart against the flow of blood. In the lung, catheters and guidewires have relatively little control at the distal end to reach specific branches of the lung and are therefore not suited for reaching these specific targets.

Insertion of a medical device, such as a cannula, catheter, guidewire or scope (broncho-, endo-, etc.), can generally produce friction and can cause tissue damage throughout the path traveled to a target. This can occur as the device is inserted into a designated anatomical region, especially when trial and error techniques through challenging anatomy cause a sawing motion. In addition, movement of the tool-tip during surgical or exploratory procedures causes motion to all of the tissue throughout the path. For example, during biopsy, ablation, cautery, electrophysiology, etc., movement of the tip of the device causes motion throughout the path of the device. This friction may dislodge vulnerable plaques leading to an increased risk of stroke, for example.

For the purposes of the present application, "Active Cannula" refers to a device which relies on the interaction of tubes to produce motion, in particular, motion at a distal end. "Nested Cannula" refers to a device constructed to result in minimal interaction between nested tubes, typically extended sequentially from largest to smallest.

Applicant's prior, co-pending application entitled "Active Cannula Configuration for Minimally Invasive Surgery," International Publication no. WO 2008/032230, Mar. 20, 2008, which is incorporated, in its entirety, by reference herein and made a part of this specification, discloses systems and methods for configuration of an active cannula device to achieve, inter alia, the interaction of multiple nested tube shapes and strengths to create a characterizable motion at a distal tip of the device. For pre-curved concentric tubes, an inverse kinematic technique is described in "Inverse Kinematics of Concentric Tube Steerable Needles" by Sears and Dupont, 2007 IEEE International Conference on Robotics and Automation, pp 1887-1892. The technique disclosed is, however, computation in free space, not considering obstacles. Inverse kinematics in this case requires identifying the specific configuration (extension and rotation) of each tube to reach a specific position and orientation of a tip. However, Configuring tubes of an Active or Nested Cannula to reach around obstacles, or be constrained by costs of traversing anatomical structures presents a significant challenge.

In order to use a Nested Cannula by sequential deployment, the configuration of the tubes must be defined so that the path and the final pre-determined position of the distal tip can be achieved.

In regard to the path, it is not sufficient to find the midline through vessels, because this information does not describe how to break down the path into extensible, common sub-components. For example, an S shape cannot be deployed simply as a single, continuous S shape. This is because as one end emerges from the enclosing tube, it faces in the wrong direction. Rather, two C shapes must be nested so that the first rotates counter-clockwise and the second, oriented 180 degrees from the first, extends to create a clockwise C. Further, it would require custom fabrication into the shapes, such as by heating, if they were each slightly different. Further, the diameter of the tubes must match the proposed anatomy.

A technique has been previously disclosed describing how a path is defined for bronchoscope control to reach a given target in 3D, while also avoiding obstacles. This technique may also be applied to bendable catheters having a pre-determined preferred arc. Planning paths to a desired target with a Nested Cannula have not been previously taught in 2D or 3D. Also, planning paths to a desired target with an Nested Cannulas using information that addresses the full range of variables that establish the location of such anatomical structure in space have not been previously taught.

Nested Cannula systems may provide some benefits over existing access and navigation techniques, including but not limited to the flexibility of the tubes associated with the Nested Cannula system, the smaller diameter relative to other navigation systems, and the sequential decrease in size of the extendable nesting design. The number of tubes in a particular Nested Cannula series and/or system is limited by the diameter of the outer-most tube and whether the succeeding tubes fit within the anatomy as they are extended. The target location(s) are generally influenced and/or determined by the needs of the surgical procedure being performed and the anatomical structure(s) in question. As a result, some highly convoluted, narrow paths and/or target locations may be difficult to reach using existing systems.

Thermoplasty, for example, may make advantageous use of a Nested Cannula system. Thermoplasty is an emerging technology used to treat asthma patients, who number about 14 million in the US. An Alair® device made by Asthmatx, Inc. is reported to be in clinical testing. Smooth muscle thickens in response to a variety of triggers, closing the airways, leading to 200,000 hospitalizations and direct healthcare costs of $5.1 billion annually. The Alair® device works by desensitizing the smooth muscle surrounding the bronchial tree.

Accordingly, a need exists for effective Nested Cannula systems and, more particularly, Nested Cannula systems that are effective to reliably reach anatomical locations based on the full range of variables associated with position of such anatomical location in space. These and other needs are addressed and/or overcome by the systems and methods of the present disclosure.

The present disclosure provides, inter alia, advantageous systems and methods for the design and configuration of Nested Cannulas for minimally invasive medical procedures. A Nested Cannula may be a customized tool called a created for a specific patient based on a pre-acquired 3D image and identification of a target location. A target location is described in six degrees of freedom comprising a location (x,y,z) and an orientation which can be determined by selecting another point relative to the first (x2, y2, z2). An exemplary system according to the present disclosure includes a plurality of concentric telescoping tubes nested within each other. The nested tubes are configured and dimensioned to reach a target location by generating a tube pathway resulting from a three dimensional image of a particular anatomical region and target location.

The target location is typically determined by the needs of a procedure being performed and the location and orientation in six degrees of freedom of the anatomical structure involved, as determined by a 3D image of the anatomical region. The requisite path is generally obtained using a three dimensional imaging system, wherein each arc is determined between an entry point and the target location or locations. The tubes are configured and dimensioned to reach relatively small and/or complex target locations within a particular anatomical region.

The tubes may be advantageously fabricated from a material exhibiting desirable levels of flexibility/elasticity. Thus, one or more of the nested tubes may be fabricated from a nitinol material. The nitinol material has 'perfect memory', in that it can be bent when a force is applied, yet returns to the originally set shape once the force is removed. Nitinol can also be used within an MRI machine, although long tubes can create artifacts. Nitinol is a relatively strong material and therefore can be made thin walled, enabling the nesting of several tubes. Tubes with an outer diameter from 5 mm to 0.2 mm are readily available in the market. Other materials might also be used, such as shape memory polymers (SMP) and other biocompatible plastics.

In an exemplary embodiment, the three dimensional imaging system is often a CT, Ultrasound, PET, SPECT or MRI, but could also be constructed from range sensors, stereo images, video or other non-medical imaging systems. Typically, the image of the particular anatomical region and the location and orientation of the anatomical structure in question is used to configure and dimension each of the plurality of tubes to define a particular shape and extension length for each of the plurality of tubes. The defined shape and extension length of each of the plurality of tubes determines whether a target location is reachable. In an exemplary embodiment, the plurality of tubes is configured and dimensioned to pre-set shapes and extension lengths for a particular anatomical region and target location and orientation. The pre-set plurality of tubes can include alternating curved and straight tubes.

In an exemplary system according to the present disclosure, the plurality of tubes are configured and dimensioned to pre-set shapes and extension lengths for a particular anatomical region and target location associated with a particular individual and the anatomical structure involved. The tubes are typically configured and dimensioned to reach relatively small diameter locations and/or locations requiring complex maneuvers within the anatomical region. The anatomical region can be any desired region necessitating an instrumental intrusion or procedure, including but not limited to pulmonary regions, thoracic regions, abdominal regions, neurological regions, cardiac regions, vascular regions, etc. The target location in the anatomical region is determined by the anatomical structure in question. There are a variety of anatomical structures or states of structures which may be in question, including but not limited to, tumors, lesions, cysts, polyps, nodules, hamartomas, neoplasms, lumps, masses, ducts, organs, tissues, wounds, tears, injuries, etc.

In an exemplary embodiment, the tubes are adapted to prevent tissue damage resulting from insertion friction by creating and/or providing a barrier with an outer tube of the plurality of tubes for those tubes nested inside. The tubes can further include a medical device member or other active structure at the tip of the distal tube adapted to perform and/or facilitate a medical procedure at a target location. Medical devices associated with the present disclosure include, but are not limited to, catheters, telescopic tips, guide wires, fiber optic devices, biopsy, suture, ablation, cautery, electro-stimulation, lavage mechanism, angioplasty balloon devices as well as other angioplasty, curatage devices, and sensors (e.g., pH, temperature and/or electrical sensors). For example, electrical sensors are commonly used to examine cardiac electrical function while fiber optic devices are commonly used to treat lesions in the lung.

The tubes can be advantageously adapted to allow manual guidance and control over the insertion of the tubes into the anatomical region aided by tactile and/or visual feedback. Positional feedback can also be used, such as electromagnetic tracking coils embedded in the tubes or within the payload carried by the tubes. The relative position can be displayed on a graphical display, preferably registered to an image. The tubes can also be adapted to allow for or interact with automated control and/or deployment systems.

The present disclosure further provides a method for Nested Cannula design and/or configuration including the steps of: (a) capturing a three dimensional image of an anatomical region and an anatomical structure in question with sufficient information so as to determine the location and orientation of such structure based upon its six degrees of freedom; (b) reading the three dimensional image of the anatomical region and structure; (c) establishing a target location by determining an effective position(s) of a distal tip of a Nested Cannula in regards to the procedure being performed and the location and orientation of the anatomical structure in question; (d) generating a series of arcs from a particular position and orientation in the three dimensional image; (e) calculating a pathway between an entry and the target location using the generated series of arcs passing through the point; and (f) generating a plurality of concentric telescoping tubes nested within each other to define the Nested Cannula, such that the Nested Cannula is configured and dimensioned to reach the target location using the generated pathway. Typically, the three dimensional image is a CT scan or an MRI image. In an exemplary method, the plurality of tubes alternate between straight tubes and curved tubes. The tubes can be configured and dimensioned to reach relatively small and complex target locations and enable an effective procedure to be performed.

Additional features, functions and benefits of the disclosed systems and methods will be apparent from the description which follows, particularly when read in conjunction with the appended figures.

To assist those of ordinary skill in the art in making and using the disclosed systems and methods, reference is made to the appended figures, wherein.

Figure 1:
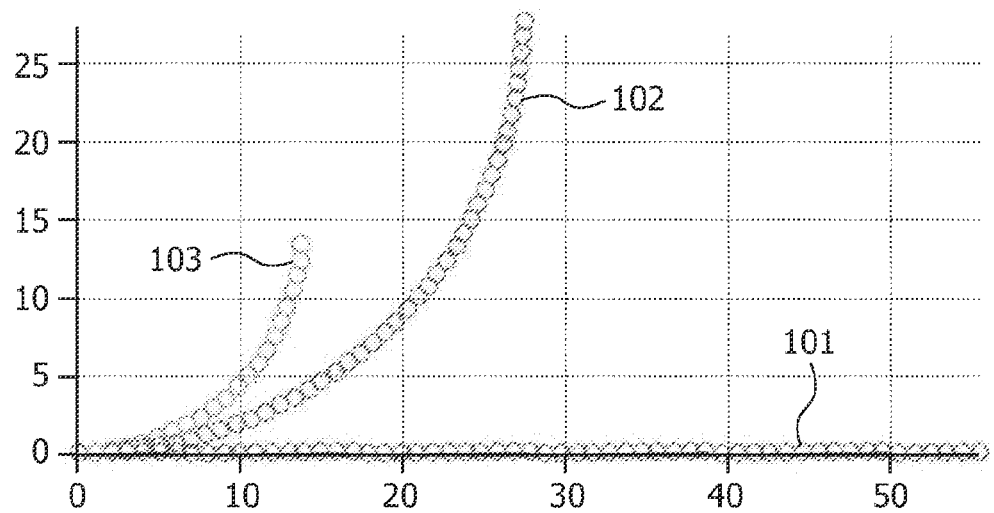
FIG. 1 illustrates three different exemplary cannula curvatures, 28 mm radius, 14 mm turning radius and straight (infinite radius)

The present disclosure provides Nested Cannula configuration systems and methods that generate a Nested Cannula customized to a patient and/or anatomical region-of-interest and/or anatomical structure in question. The disclosed systems and methods advantageously enable minimally invasive surgical procedures to reach particular target locations that are commonly difficult to reach by traditional surgical means. Nitinol tubes allow for flexibility and dexterity to reach complicated and challenging target locations. One or more 3-D images are used to determine an effective target location and to generate a series of 3-D paths that define the shape and extension length of the flexible tubes. In an exemplary embodiment, target location(s) and tube paths are computed within a few minutes. Configured Nested Cannula systems and methods allow for complex vasculature to be traversed faster than manually shaped catheters that typically require trial and error to be formed correctly. Configured Nested Cannula systems and methods also allow for more effective treatment as compared to manually shaped catheters or other methods which are unable to reach location(s) required for effective treatment.

The motions required to reach a target are designed into the tool so it can perform multiple turns without the additional size or weight of motors, control wires, etc. The disclosed miniature, dexterous tool can thus provide accurate, minimally invasive reach into very small anatomical areas and/or regions.

According to the present disclosure, Nested Cannula systems include a plurality of telescoping, pre-shaped tubes. Concentric telescoping tubes made from flexible nitinol (nickel-titanium alloy) or other suitable material are generally extended along an anatomical region, each tube having a particular curvature. Nitinol is a particularly desired material for cannula fabrication due to its memory attributes and flexibility, thus enabling a tube to conform into a larger tube surrounding it until the tube is extended. Typically, the largest tube is first introduced into a desired region followed by the introduction/extension of successively smaller tubes to an expected/desired length and orientation. In an exemplary embodiment, tubes may be made of rubber or plastic which is less expensive but may require thicker walls. Non-metallic fabrication may be advantageous if the number of tubes required is sufficiently small that they can reach the target position, or the anatomy is large enough to accommodate each tube. The characteristics of tubular elasticity is also important; therefore, it may be advantageous to nest the tubes near to the time that they are deployed so they have less chance to take on a new shape or otherwise suffer from a memory effect.

An exemplary Nested Cannula according to the present disclosure typically includes a plurality of telescopic nitinol tubes (often referred to as a series of tubes) operable to reach into relatively small and/or complex locations in a desired anatomical region.

Thus, an exemplary system according to the present disclosure includes a Nested Cannula, wherein the shape and extension distance of each tube necessary to reach a particular target location is configured and dimensioned from an image of a particular anatomical region. The target location is determined by or otherwise based upon the surgical procedure being performed and the location and orientation of the anatomical structure in question. Typically, images used for Nested Cannula configuration and target location determination are derived through medical imaging systems, such as a CT or MRI system. An exemplary Nested Cannula system associated with the present disclosure is also operable to determine whether a particular target is reachable by a plurality of tubes of a Nested Cannula.

According to a particular embodiment, a Nested Cannula system includes a "standard set" of tubes alternating between curved and straight tubes. Using the "standard set" allows for reaching various locations within a given anatomical region without the cost or delay of custom manufacturing of each particular tube.

The present disclosure also provides an exemplary method for configuration of a Nested Cannula system. A particular 3-D image of a target anatomical region and structure in question is generated using an imaging system, such as CT, Ultrasound, PET, SPECT or MRI. These images may be registered to each other, creating a multi-modal image, such as PET-CT, where the PET provides critical information on the target and surrounding relative anatomy and the CT image can be segmented to define forbidden, 'critical regions' (i.e., regions where the Nested Cannula may not travel). A point, typically the target location, is first defined. This location is determined in regards to the surgical procedure being performed and the location and orientation of the structure in question. A point can also potentially be an entry or a central key point. Starting at an entry point, reachable locations are calculated and a correct set of telescoping tube shapes required to reach the 3-D target locations are determined. Based on such determinations, the individual tubes are selected and/or generated.

The following are examples associated with the present disclosure, whereby each of the components of the framework is described:

(A) Method

In the following sections, several key components of a framework will be described and then specified for an exemplary Nested Cannula application associated with the present disclosure including: a discretely-defined configuration space, forbidden states, start or goal state(s), neighborhood and cost metric.

1. Configuration Space:

The configuration space is defined by the span of possible parameters that describe the state, sometimes called the 'configuration' of the device. For example, a robot configuration can be defined by the angle value of each joint. The span of all possible joint angle configurations forms the configuration space. Similarly, a vehicle's configuration can be specified by its x,y position and orientation. At each state, often an array entry specified by the parameter values for one device configuration, several values are stored, including the direction to proceed from this state to the next and the remaining cost to reach the goal from this state. These values are assigned by a search method, performed later.

The configuration of a Nested Cannula (Nested Cannula) may be represented by the x,y,z location and rx,ry,rz orientation of the Nested Cannula's tip, resulting in a 6 dimensional problem space. Relevant locations may occur within an exemplary 512×512×295 pre-procedural CT image, with exemplary x,y,z resolutions of 0.078, 0.078 and 0.3 respectively. Discretizing all orientations at 10 degree increments for the CT image would require 3.6 trillion states, each containing about 40 bytes, for a challenging memory requirement of 144 terabytes. After the remaining four components are explained, the technique is explained that enables the use of a configuration space that is on the order of the size of the 3D CT image.

Figure 7:
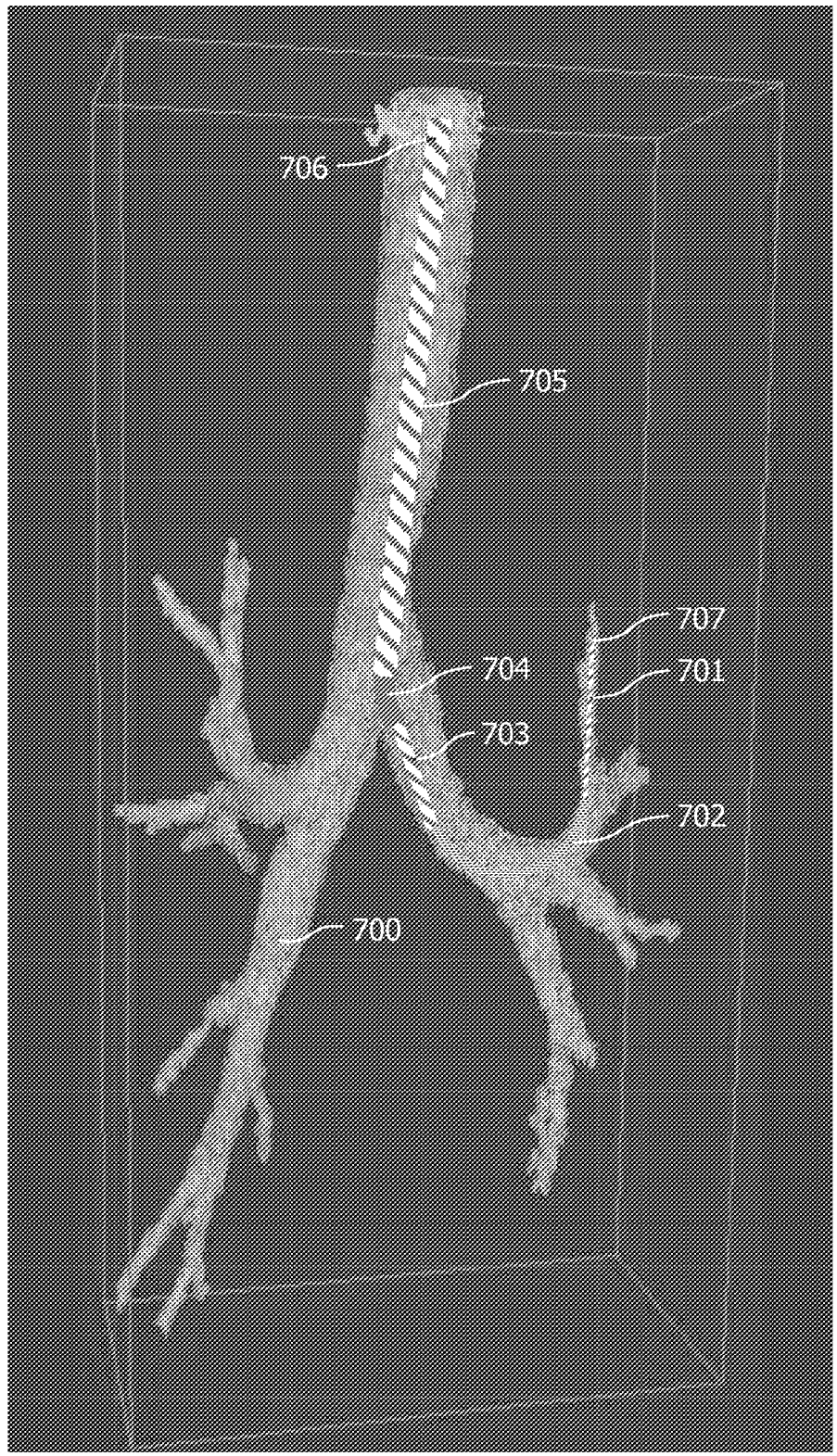
FIG. 7 illustrates a segmentation of lung air passages and an exemplary configuration of tubes associated with the present disclosure.

2. Forbidden States:

The anatomy is segmented so that some voxel regions are considered 'free-space' states and others are forbidden regions through which the device must not pass. This segmentation step can be performed by many different techniques, including manual drawing, model based segmentation where the user places a nominal model in the area of the anatomy and a computer refines the segmentation, or fully automated segmentation. In this example, configuring a Nested Cannula for the lung requires segmentation of the lung airways. The example image in FIG. 7 is segmented using a semi-automated Fast March (A*) method with a threshold. This generates an interior free-space volume, and an external forbidden volume (lung tissue).

3. Start or Goal State(s):

The location (x,y,z) and orientation (rx,ry,rz) or (x2,y2,z2) of a point of interest represents a target state (goal) and can be selected as a seed point for the search (described later). This target state (location and orientation) is typically determined based upon the surgical procedure being performed and the location and orientation—which may be in six degrees of freedom—of the anatomical structure in question. Naturally, if the entry direction is rotationally invariant, such as if the tube carrying a tool (such as a light) functions equivalently well in all rotations, then a specific direction for 'up' can be assigned by the system. Alternatively, the entry position, such as a state within the trachea, can be used as a seed point for the search.

Figure 8:
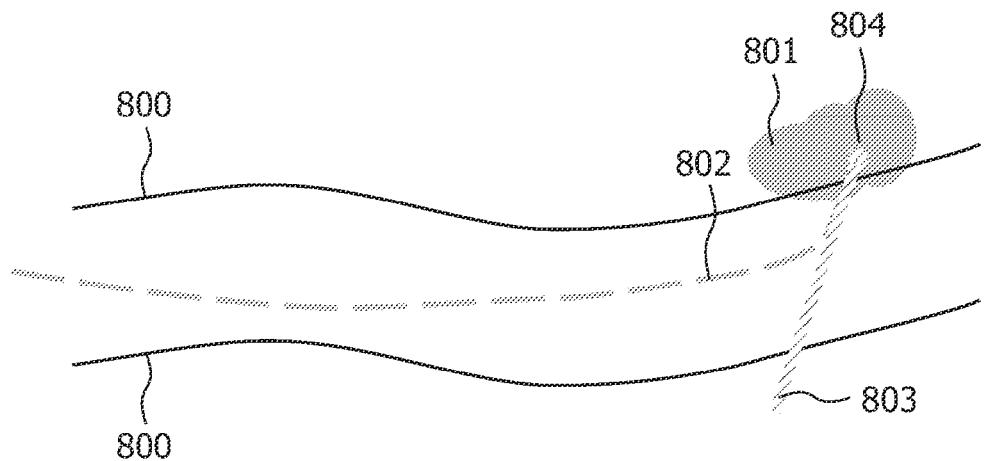
FIG. 8 illustrates an exemplary approach angle to a lesion intended for biopsy.

In a preferred embodiment, the start or goal is selected based on where the relative free space is smaller (more constrained). From this location, an entry angle may be defined that is clinically suitable. For example, with reference to FIG. 8, airway 800 contains a lung nodule or suspicious mass 801 targeted for biopsy. For present purposes, the nodule or mass 801 represents the anatomical structure in question. The objective is to find a path 802 that penetrates the central area of the lung nodule or suspicious mass 801, reaching the target state 804 where the angle of insertion, also called the target approach angle 803, is substantially perpendicular so that the force of the needle at the puncture site is directed inward. In this case, the preferred angle may be a compromise relative to the ideal perpendicular orientation, but addressing the constraints of the limited vessel size by angling toward the larger airways (to the left) from which the Nested Cannula will arrive.

Figure 9:
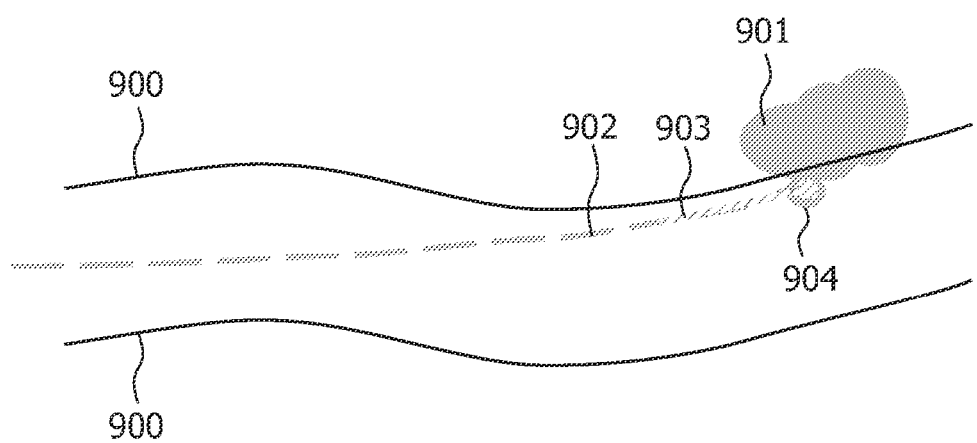
FIG. 9 illustrates an exemplary tangential approach angle to a lesion intended for BronchoAlveolar Lavage (BAL).

In other situations, such as schematically depicted in FIG. 9, the target approach angle 903 in an airway 900 can be more tangential, possibly not even touching the surface of the lung nodule or suspicious mass 901 to the target state 904. This approach may be clinically useful, such as when performing a BronchoAlveolar Lavage (BAL) procedure in the lung, for example. The target state 904 is reached via the proposed path 902. BAL is a process of infusing and re-aspirating sterile saline solution (typically 0.9%) in distal segments of the lung via a fiber optic bronchoscope. The solution fills the airspaces distal to the tip of a bronchoscope. The re-aspirated solution can be used to differentiate malignant from benign nodules identified on CT by assessing the aspirated cells. However, the sensitivity of the BAL procedure varies, meaning actual disease may not be detected. One possible reason for this variable sensitivity is that the tip of the bronchoscope cannot reach sufficiently far into the lung; therefore, more fluid than necessary is used to fill the distal area, reducing the chance that actual diseased cells are detected.

If a Nested Cannula is used, however, and a smaller portion of water is delivered to the lung region, suspicious cells may be detected more easily because they will be present in a higher relative concentration. After a bronchoscope-based BAL procedure, fluid remains and must be absorbed by the lung or expectorated. After a Nested Cannula BAL procedure as disclosed herein, less fluid will generally have been delivered to the lung region, thereby causing fewer post procedural side effects. Additionally, the ability to reliably, efficiently and specifically deliver the Nested Cannula to a target location may not only translate to an enhanced indication of disease presence, but may also be effective to confirm disease location.

Figure 10:
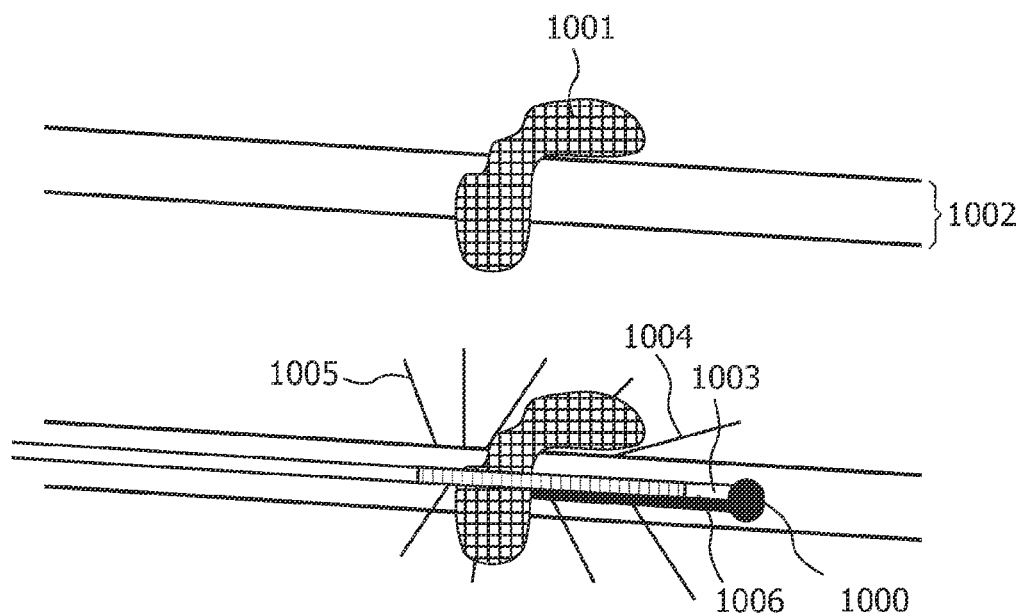
FIG. 10 illustrates photodynamic therapy of a lesion located and orientated around a vessel or air passage in a lung.

In other situations, such as schematically depicted in FIG. 10, a vessel or air passageway 1002 is surrounded by lung lesion 1001 and is targeted for photodynamic therapy (PDT). The lesion 1001 represents the anatomical structure in question and 1000 represents the target state (position and orientation of distal end). The target approach angle 1006 is tangential and may not touch the surface of the lesion 1001 to the target state 1000. The approach angle can be determined based on the location and position—in six degrees of freedom—of the anatomical structure in question in order to facilitate effective treatment. This may be clinically useful, such as when performing a PDT in the lung. In this exemplary case, the target state 1000 was selected in regards to the surgical procedure being performed (PDT) and the location and orientation in six degrees of freedom of the anatomical structure in question (lesion 1001). The target state 1000 and approach angle 1006 were chosen because lesion 1001 is located around vessel 1002 and the light radiating 1005 from diffuser 1004 located along fiber 1003 is within an effective distance from lesion 1001. In this situation, the objective is to find a path that penetrates lung vessel 1002 reaching the target state 1000 with a target approach angle 1006.

Figure 11:
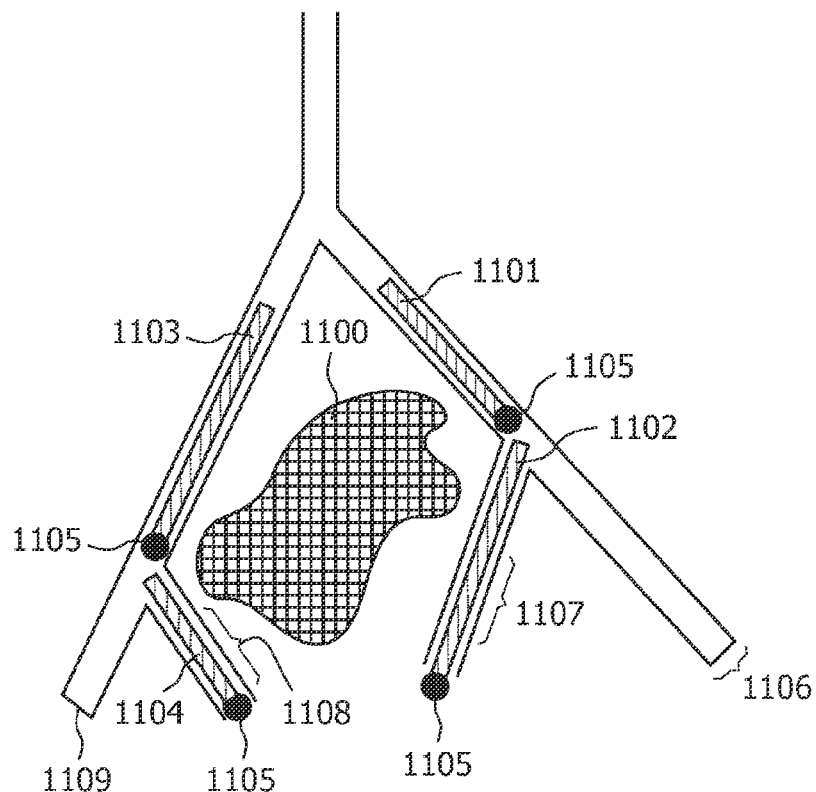
FIG. 11 illustrates photodynamic therapy of a lesion in a lung not located and/or orientated around a vessel or air passage.

In additional situations, such as schematically depicted in FIG. 11, lung lesion 1100 is targeted for PDT treatment, but the lesion is not surrounding an air passageway or vessel. Lesion 1100 represents the anatomical structure in question and 1105 represents the target states (positions and orientations of distal end). In this situation, the lesion 1100 must be attacked from two or more locations. The lesion coverage must be divided based on the reach of nearby vessels 1106, 1107, 1108 and 1109. The target states 1105, appropriate approach angles and diffusers 1101, 1102, 1103 and 1104 are computed according to the present disclosure based on the location and position in six degrees of freedom of lesion 1100 in order to facilitate effective PDT.

Of note, it may be that a tube cannot reach a particular region based on the size or visibility of the available airway or the complexity of navigation. For instance, the planner may find that the Nested Cannula cannot reach a particular location, such as the fairly tight constriction in 1107. By having a configuration mechanism, the Nested Cannula design, target location(s) and specifications of the instrument inside the cannula assure maximal coverage and destruction of lesions, e.g., lesion 1100.

Similarly, a series of locations can be defined for deploying thermoplasty. In this case, a set of tubes is computed for distal location. The thermoplasty element is first delivered to the distal location, and as the thermoplasty is carried out, a nested cannula is retracted by the therapeutically recommended distance for the specific probe. Each cannula is retracted in reverse order; however, the innermost element, carrying the active device is left extended.

4. Neighborhood:

The neighborhood encapsulates the set of fundamental device motions that can be performed in free space based on the available controls and mechanical properties of a device. The curvature for a particular tube has a specified 'minimum turning radius', similar to a car. In the example shown in FIG. 1, three different curvatures are considered for the Nested Cannula. The first curvature 101 is straight (no curvature, or equivalently, infinite turning radius), the second curvature 102 has a 28 mm turning radius, and the third curvature has a turning radius of 14 mm. The series of points shown along curvature 102, for example, demonstrate the position in X,Y space for a particular extension of the 28 mm curved tube. The tangent of this position gives the orientation. For a Nested Cannula, the primary controls are rotating and advancing each of the tubes, where the curvature of each tube is preselected from among a set of discrete curvatures, such as the three described/depicted in FIG. 1.

Figure 2:
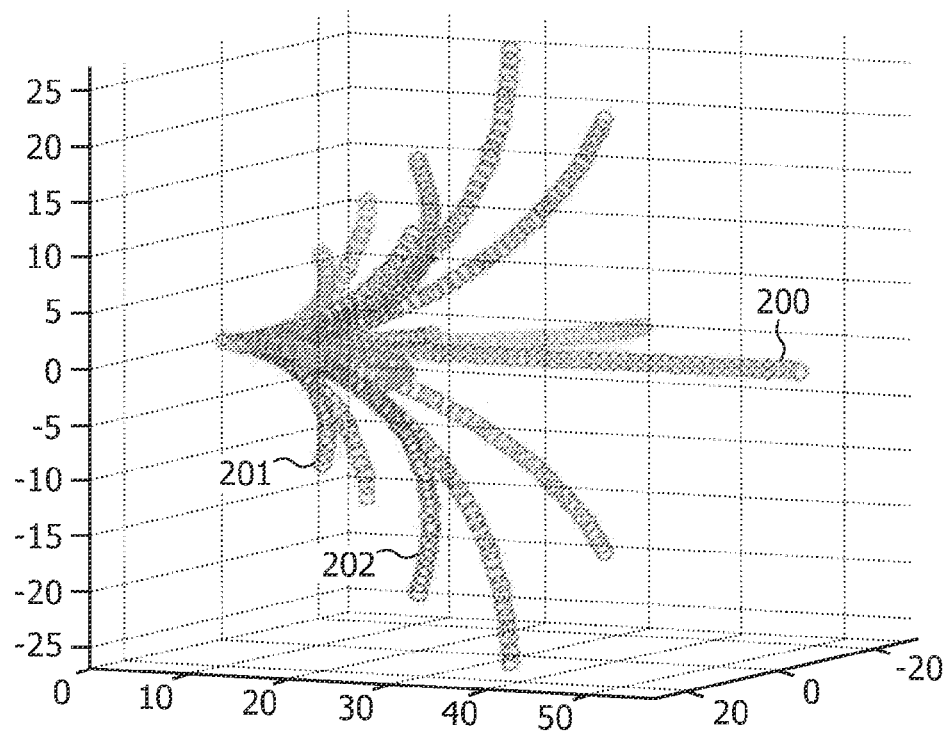
FIG. 2 illustrates an exemplary 3-D neighborhood of arcs, representing options of travel for the center of each tube associated with the present disclosure.

By rotating each of the three arcs illustrated in FIG. 1 in 45 degree increments, the resulting neighborhood can be illustrated as in FIG. 2. Each curved tube at a specific rotation is sometimes also called a fiber. In FIG. 2, there are 8 rotations for the two curvatures (14 mm and 28 mm turning radius), plus an additional option (straight with no rotation). One example is highlighted for each curvature, a 14 mm turning radius fiber 201 and a 28 mm turning radius fiber 202, for the same rotation. Each of the fibers can be extended to any length, following the same curvature. The length of the arc for a non-holonomic problem with an arbitrarily discretely-defined space performs advantageously if a curved fiber is extended until the orientation is changed by 90 degrees, as shown in FIGS. 1 through 6. The straight portion of the neighborhood 200 ignores the rotational component and assumes that the incoming rotation maintains the same, since a straight tube at an arbitrary rotation follows the same path. It is noted that although FIG. 1 and FIG. 2 appear to have rectangular pixels, it is but a byproduct of the selection of axis markers.

The neighborhood for the Nested Cannula is the mechanism that encapsulates the non-holonomic behavior of the device. Non-holonomic means that specific values for the control parameters (advancement plus rotation) do not uniquely define a resulting position and orientation without knowing characteristics of the path already taken. The neighborhood is a key component of a search (described later) because it captures the set of permitted motions from a location.

5. Cost Metric:

For each of the neighborhood states, a cost is assigned. This is the constituent cost for a local move based on the overall optimization criterion. In the Nested Cannula example, it is desired to minimize the distance traveled. Therefore, the distance traveled along the arc or straight path from a home location to a neighbor defines the cost.

(B) Conversion of 6D to 3D Configuration Space for Tractability

The discretely-defined configuration space above, requiring 144 terabytes, not only causes a memory problem on most computers, but as disclosed herein, requires a search through these states. Proceeding with this framework requires a modified technique that reduces the configuration space and computation time.

Two observations drive this modification. The first is that the forbidden region derived from the 3D CT remains the same regardless of the orientation of the tip. It is therefore useful to identify conditions under which the 3D orientation can either be ignored or reduced to a few values stored per state, within the 3D space.

The second observation results from reviewing the primary objective of the configuration space, which is to store the values describing the current state and provide directions to the next state. If an orientation can be fixed at either the start or the goal seed location, this provides an anchoring basis for calculating unique, neighboring orientations. From this seed position and orientation, positions with specific orientations can be calculated for all reachable points.

Planned orientations rx,ry,rz or x2,y2,z2 can then be stored as values within each x,y,z configuration state along with cost and direction. Orientation rx is encapsulated implicitly in the neighborhood as a thread number (thread number defines relative orientation of each thread, FIGS. 2: 201 and 202). In Cartesian coordinate system (XYZ), orientation ry is rotation around Y axis, and orientation rz is the rotation around the Z' axis, where Z' axis is Z axis rotated around the Y-axis for angle θ. Rotations around the Y-axis is described with angle θ. Rotation around Z' axis is defined by angle φ. Thus, parameter set {rx,ry,rz} can be replaced by parameter set {thread, θ, φ}. Eliminating {thread, θ, φ} as independent parameters of the configuration space, reduces the space from 6D to 3D, dramatically reducing the storage space required to about 77 million states and a more tractable 3 gigabytes of memory.

Positional (X,Y,Z) discretization error can also be reduced by storing the planned values within each state. The inherent (default) value of the discrete state is the value represented at the center of the voxel. Depending upon the level of discretization of the voxel, this value may be sufficient for controlling the proposed device. Further improvement may be achieved by optionally storing the precise positional (X,Y,Z) values within the state rather than incurring the discretization error throughout the configuration space. There are two specific advantages to this technique.

The first advantage is that the location can be stored to arbitrary precision for the position. This storage ability can be particularly helpful when the dimensions of the voxels are not equal, which cause high precision in some directions (e.g., X and Y) with lower precision in other directions (e.g., Z). For example, in a medical image such as in a CT, the voxels may be non-square or more properly, non-cubic or anisotropic, where the X and Y voxel length may be (0.078 mm) and the Z voxel length (0.3 mm). Although the obstacle coverage is defined with a resolution of voxels, the control can be more precisely defined by storing the computed (e.g., double precision) $x,y,z$,thread,$\theta$, $\phi$ values within each state space.

The second advantage is that if the current state is not adequately controllable to the next state, then this limitation may be identified and automatically trigger alternate control strategies. In the simplest case, the device may stop and may wait for the proper, safe conditions to resume motion. For example, while a patient is breathing, the x,y,z of the actual position of the device will move. It may be appropriate that only when the actual position is within 0 5 mm of the planned scenario, then device control may proceed.

Once these key components are defined, the shortest, collision-free path can be generated from a fixed seed (start or goal) based on the set of available component tube curvatures or shapes and motions permitted with that tube (such as rotation and extension) which are encapsulated in the neighborhood. The path consists of concatenated arc or straight motions between the start and goal, and is carried out step-by-step with associated controls.

(C) Path Generation:

An A* search method is used to find all possible paths from the seed location(s). The 3D search has been previously described, including for vehicle maneuvering and bronchoscope maneuvering. The same 3D search is performed for the Nested Cannula, but will be illustrated in 2D due to limitations of the paper medium.

Figure 3:
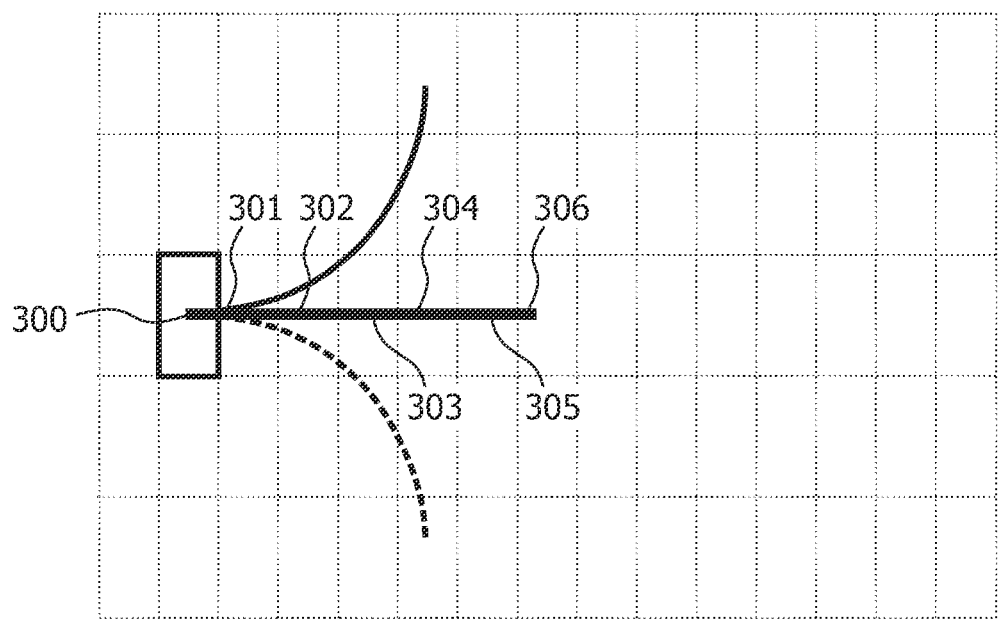
FIG. 3 illustrates an exemplary 2D neighborhood of arcs highlighting the neighbor arcs in the straight direction.
Figure 4:
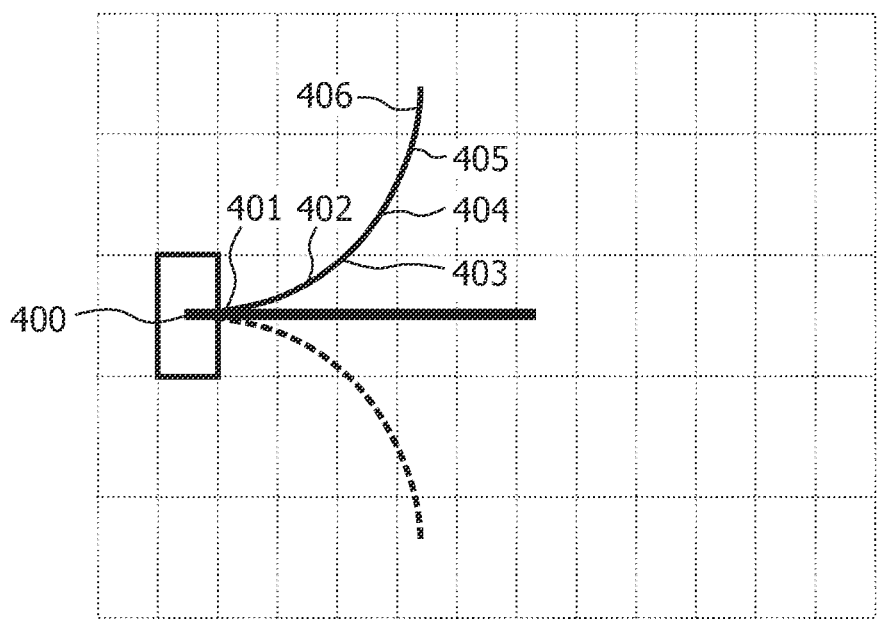
FIG. 4 illustrates the exemplary 2D neighborhood of arcs of FIG. 3 highlighting the neighbor arcs along a fixed curvature to the left.

FIG. 3 shows an exemplary 2D neighborhood. This simplified neighborhood shows a 'home position' 300 and a straight thread, including neighbors 301-306. There are also two threads having the same curvature, conveniently set at 180 degrees rotation from one another so that they lie on the same plane of the paper. In FIG. 4, the home position 400 corresponds to the home position 300 in FIG. 3, and neighbors along the left thread are identified 401-406. An equivalent set could be identified along the right thread.

Figure 5:
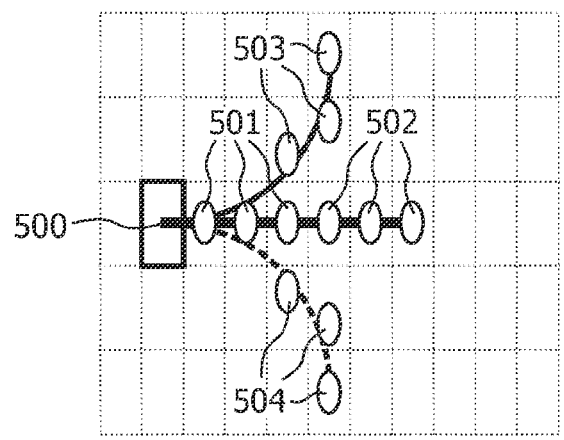
FIG. 5 illustrates the exemplary 2D neighborhood of arcs of FIG. 3 identifying the optimal neighbors from each fiber of the original set.

The neighborhood governs the locations considered as subsequently reachable neighbors, rather than considering only those that are adjacent. The states are expanded sequentially in a least-cost-first manner, adding the transition cost to the total cost so far, and storing only those that are minimum. The revised tip orientation is calculated based on the prior orientation and the change incurred by traveling to the selected neighbor. In FIG. 5, the neighbors ultimately reached with a minimum distance metric are shown. The neighbors reside in a non-cubic configuration space, which further highlights how a minimum cost to a state is identified. In this case, the neighbors comprised of 501 and 502, are reached via a straight path. The neighbors reached along the left fiber where there is not a more optimal (e.g. straight) path to these states are identified as 503. Similar neighbors can also be identified along the right fiber as 504. These neighbors become open nodes for subsequent rounds of expansion.

Figure 6:
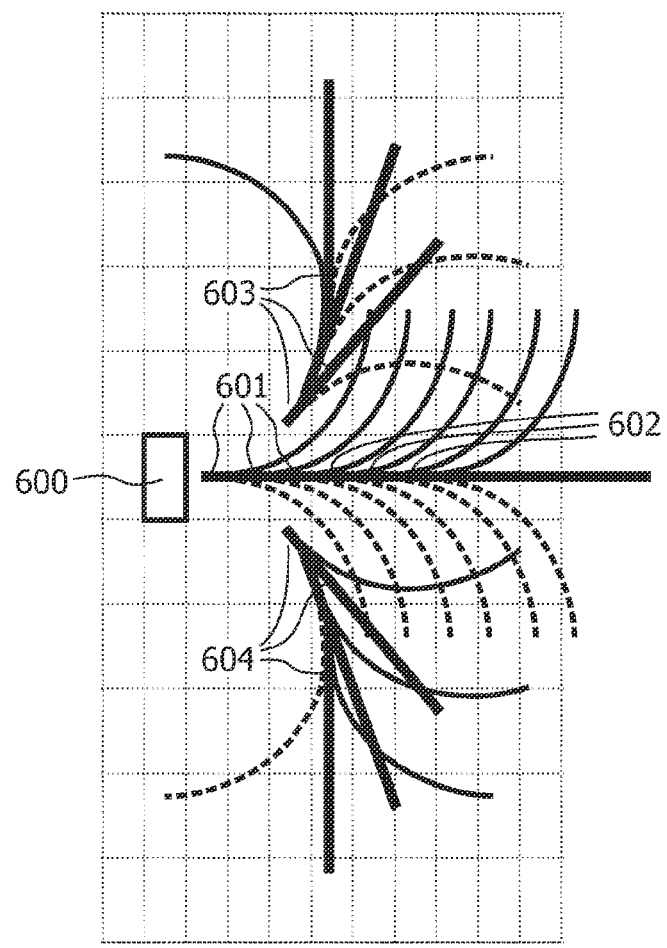
FIG. 6 illustrates coverage resulting from the expansion of a first set of opened neighbor arcs and concatenating of arcs.

In FIG. 6, the original home node 600 is shown, along with an illustration of the pattern of neighbors that would be expanded at the locations and orientations described in FIG. 5. At each 'open location', the home node 600 orientation is read, and the subsequent expansion is oriented with respect to that orientation. The positions and orientations of the set of open neighbors 503 from FIG. 5, are expanded at locations 603, with a new neighborhood oriented to match the open node's home orientation. Similarly, the open nodes of 501 and 502 of FIG. 5 are expanded at locations 601 and 602 of FIG. 6, and the open nodes of 504 in FIG. 5 are expanded at locations 604.

This simplified search example so far assumes there are no forbidden states. The expansion of a neighborhood is preferably performed from the home location of the neighborhood along each fiber from nearest to farthest. If a forbidden state is discovered, then the remainder of the fiber is considered unreachable and the search continues with the next fiber. This prevents the path from 'jumping over' a region that is illegal.

The same search technique, including the sequential search through the fibers to avoid obstacles is performed in 3D. It requires only that the neighborhood shown in FIG. 2 is re-oriented to a given position and orientation of an open node to calculate the set of subsequently reachable states. The process terminates when the successive computations either fill the space (when there are no more open states) or the search reaches another acceptable termination-state. A set of acceptable termination states for example may be any node along a plane of the uppermost trachea, when the search starts from a target such as target state 804 of FIG. 8.

An intuitive analogy for this least-cost-first A* expansion follows. Imagine a wave generated by a pebble dropped in a pond at a seed location. As the waves ripple out, propagating around islands (forbidden regions) a snapshot is taken every second, including a timestamp ($t_0 \ldots t_n$). Drawing a perpendicular to the waves on the snapshots forms a 'pointer' that gives directions from every reachable location toward the source seed. From any reachable location, one needs only to follow the pointers from location to location to reach the seed location where the pebble was dropped. In addition, the timestamp on the image containing the current location indicates the estimated time required to travel back to the seed. Whenever a location is not reached by the waves, there is no path between this location and the seed location. Identifying situations that produce no viable path (using a specific device) is a useful property, since it saves time and energy in a needless struggle. When there is no path, other devices can be modeled to find one that is effective. Another approach is to identify whether one or more obstacles can be moved. Although this analogy is described in 2D, the A* method works as well in 3D or higher dimensions. Several efficient A* techniques, known to one of skill in the art, may be used to focus the search so that only the most likely states required for the solution are calculated.

(D) Path Following:

If a termination node is reached, then a path is computed between the termination node and the seed. Alternatively, a user or computer can select the end point to be connected to the nearest seed. The path is generated state to state, between the start and goal. Following from one state to another requires reading the 'direction vector' which might be stored as a neighbor number. As shown in FIGS. 3 and 4, the neighbor number also indicates the fiber, and therefore the type of path taken. For example, a neighbor located at 405 in FIG. 4 identifies that a specifically curved arc was directed left a particular distance, resulting in a particular location and orientation. This corresponds to the rotation within the enclosing tube and insertion length required for this curved tube to reach the next state along the path.

In FIG. 7, an example path is shown between the entry at 706 and the target 707. In order to calculate the number of tubes correctly, if a fiber leads to the same type of fiber (having the same relative orientation and curvature) along the path, it should be considered one continuous tube. In other words, arcs having the same curvature and relative rotation can be concatenated to become a longer tube with the same specification, for example two 28 mm radius arcs at +45 degrees rotation. Each change in thread type in the series represents a change to the next tube in the nested series of tubes of the Nested Cannula system. The path given in FIG. 7 is a schematic in order to simplify the visual results. It is noted that the tube must pass through the nose or mouth to reach the trachea and consider the path from the entry point 706, which has a specified orientation.

The first tube is straight and must advance the length of 705. From this point a second tube 704 is advanced until it reaches where 704 connects to tube 703. This second tube 704 has a narrower outer diameter than the inner diameter of 705 and has a curvature specified by the neighbor and fiber selected. In a similar fashion, 703 is straight and extends until it reaches 702, and 702 is curved, extending until it reaches 701. Each successive tube is smaller than its predecessor.

(E) Defining Tube Radius for a Particular Function and Anatomy

A path is viable only if the series of tubes can actually fit inside a specified region. A challenge is that anatomy can be complex, varying in diameter throughout. Also, the more types of maneuvers required, the more tubes that are generally required, and the larger diameter that may be required at the entry. Several methods are presented to generate tube diameters based on the given path and free-space available.

1. The brute force method is to create the path, and compute the required tube outer diameters for each section of tube, starting from the smallest. For each point along the path, test for illegal states between the point and a radius distance. If there is an intersection, the path is not viable, however without some additional methods this leaves the viability to luck.

2. A more reliable method is to shrink the free-space by the size of the largest tube expected. In this method, every path can be realized because it is within the boundaries. Unfortunately, this technique will also cut off access to anatomy that could be reached by small tubes.

3. A potentially less reliable method is to shrink the free-space by the size of the smallest available tube's outer diameter. This immediately delineates the regions where no access is possible even with the smallest tube, and regions of free-space that continue to offer some potential. Planning in this space improves the chances of identifying a viable path, but still does not guarantee it.

4. A preferred method has several key steps:

4.1 Pre-compute several versions of the forbidden region. Each forbidden region is grown by the outer radius of each useful tube A tube is useful only if it nests with the other tubes and the smallest is large enough to carry the intended payload or tool. The intended use of the Nested Cannula determines the smallest useful tube. For example, if a camera is to be inserted, it will be larger than if a fluid sample is to be taken and the tube is empty. Eroding free-space, or equivalently, dilating the forbidden space, can be performed rapidly, and only once for each useful tube. Dilation and Erosion are well known from image processing.

4.2 Choose the seed within a narrow part of the anatomy along the path. In the lung therefore, a particular seed is likely to be a distal tumor location rather than the center of the trachea. In the brain, the narrowest vessel should be chosen, such as an ophthalmic artery rather than the carotid artery for example. Although this is typically located at the target, it is possible to be between the target and the entry point such as in a vascular application where there is plaque buildup midway.

4.3 Set the forbidden region at the seed to be determined by the outer radius of the smallest useful tube.

4.4 Track the total number of tube changes that have occurred since the seed location. This can be stored in the configuration space in addition to the cost-to-goal. When a node is expanded, the forbidden region is selected based on the number of tube changes, which defines the radius of the current tube used.

When a terminating node is reached, the radius of the required tube will also be specified. The use of a Nested Cannula system according to the present disclosure allows clinicians and/or other medical personnel to reach/access relatively small diameter target locations and/or target locations requiring complex maneuvers within a particular anatomical region.

An exemplary anatomical region includes the thoracic region, although many additional anatomical regions may benefit from the disclosed systems and methods. An exemplary Nested Cannula system associated with the present disclosure is operable to reach target locations that are generally unreachable by a bronchoscope or endoscope.

An exemplary method according to the present disclosure for controlling an Nested Cannula system to solve non-holonomic problems includes generating a series of arcs defined from a particular entry point to a particular target of a desired region. The series of arcs form a desired pathway within the region.

An exemplary Nested Cannula system according to the present disclosure can protect against tissue damage resulting from tube insertion friction. A nested design allows the outer most tube to protect tissue contacted near the insertion point. This can be particularly helpful during insertions associated with lung-related procedures or where vascular plaque may be unstable. An exemplary Nested Cannula system includes a series of tubes configured and dimensioned to a particular shape, length, maximum diameter and sequence that are determined through 3-D imaging calculation methods.

Nested Cannula technology offers several advantages over other navigation devices including, but not limited to: (i) effective control and angulation of a telescopic tip without the use of joint motors or marionette wires; (ii) smaller tube diameter than traditional devices; (iii) cannulas that are relatively inexpensive and typically disposable; (iv) nitinol and similar fabrication materials allow for cannulas to be formed into arbitrary shapes and curvatures, thus facilitating entry and/or access into complex regions; (v) nitinol is an MRI-friendly material; (vi) pre-formed cannula configurations can be guided manually with the assistance of image guidance and later controlled by MRI-friendly piezo-motors; (vii) successively smaller concentric cannulas match various shapes for use in various medical applications which enter a larger region and ultimately reach to successively smaller regions; and (viii) early deployment of a cannula system can be achieved with manual control and accurate calculations of configurations.

Alternative Embodiments

According to an exemplary system, a standard set of cannulas can be defined such that a plurality of target locations in an anatomical structure, a lung for example, can be reached using particular pattern of tubes but custom deployed at particularly calculated angles and lengths for a particular patient and/or target location. A series of arcs and straight tubes can be calculated that reach a particular target location. Target tube paths are generated from the resulting series of arcs and straight tubes. The path calculation may be weighted such that a change from one fiber to another incurs an additional penalty.

Figure 13:
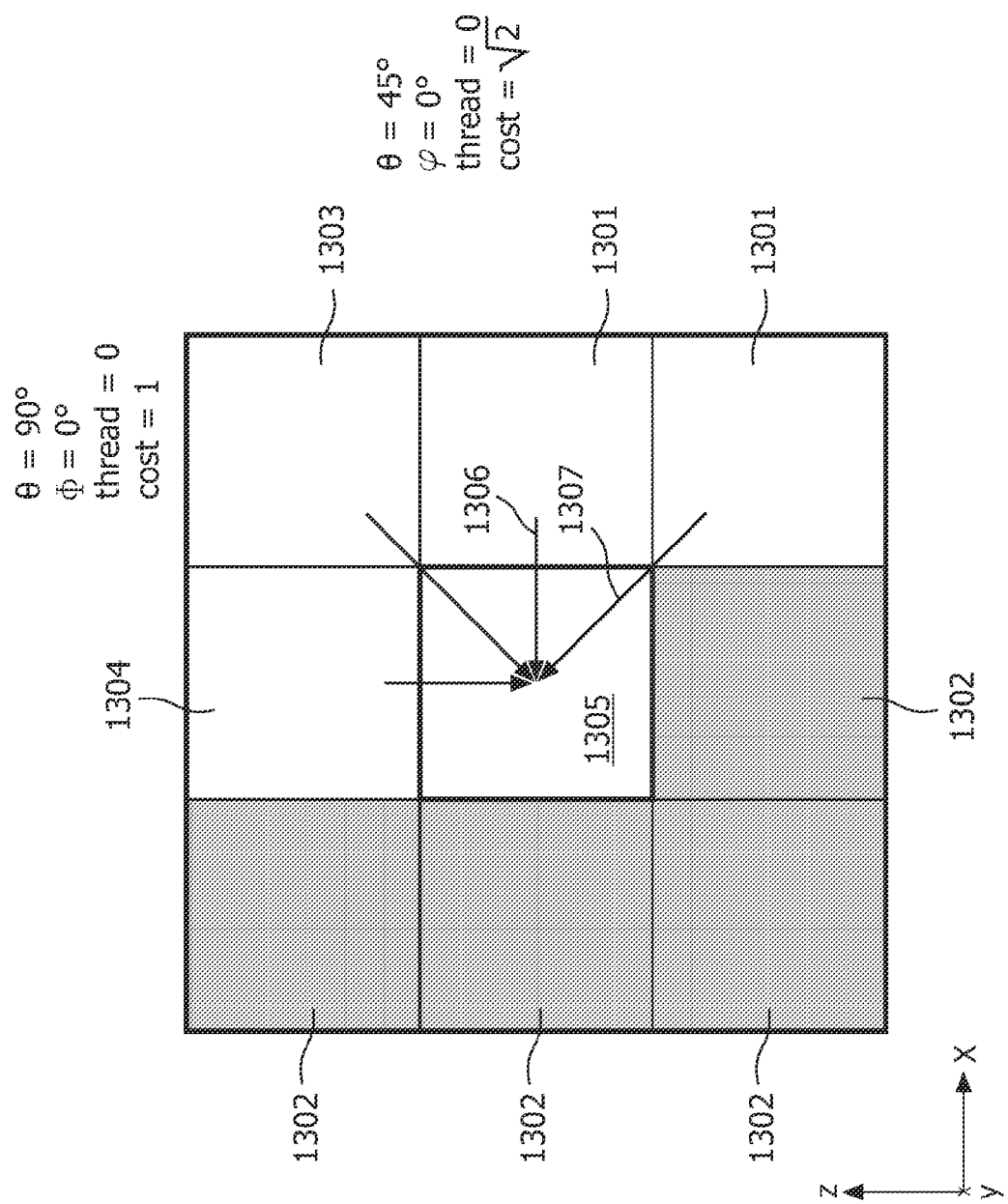
FIG. 13 illustrates a two dimensional cross-section of three dimensional states surrounding a selected target point.

It can be simpler for the physician to select a target point, often in 3 (x,y,z) dimensions without defining the entry angle. The system can compute entry angles automatically based on the entry direction from adjacent nodes toward the target point. The point can be selected from a set of 3 orthogonal views, for example coronal, axial and sagittal. For simpler representation, FIG. 13 shows a 2D slice of the 3D states surrounding a selected target point 1305. Rather than adding the selected target point to the heap as a seed for the search, the surrounding states are considered as potential seeds. From the selected point 1305 in FIG. 13, a set of surrounding states are analyzed for automatic inclusion in the search heap. Surrounding neighbor states may include 'illegal states', typically having infinite or very high cost, for example, the shaded states labeled by 1302. Other states are passable such as those identified by 1301, 1303 and 1304. Analogous procedures are performed for all of the surrounding states in 3D, including those not shown. The analysis includes two basic steps for each surrounding state:

(1) Determine whether the path to the goal is permitted, that is, passable at some cost, using a specific transition or thread-type. For example, a straight motion, thread 0, can be used. If there are no 'illegal' or 'infinite cost' states intervening, then the path is permitted. Obviously paths are permitted from an adjacent state 1306 to the selected point 1305. If a diagonal neighbor 1303 is passable, it is only passable if at least one of the horizontal 1301 and vertical neighbors 1304 are passable. If both are not passable (i.e. illegal), then the diagonal is not permitted, since it cannot be reached with certainty. It may be preferable, to require that both the horizontal and vertical neighbor are passable before permitting the diagonal.

(2) If the path is permitted, then store the cost to the goal, the thread used to reach from a given neighbor to the target 1305, define the angles for Theta and Phi, and add this node to the search heap. The two angles and the thread, as shown for 1303 and 1304 provide the full 3D orientation. The angles represent the rotation of the neighborhood's frame of reference, and the thread represents the movement in a given direction.

Having a pre-set pattern enables the potential reuse of the same Nested Cannula system extended to different lengths to reach different target locations in the same individual in the same procedure. Predetermined shape and extension distance patterns for a particular patient can significantly reduce costs associated with a particular medical procedure.

According to an exemplary system, a standard set of cannulas can be defined such that a plurality of targets, in a lung for example, can be reached using particular pattern of tubes but custom deployed at particularly calculated angles and lengths for a particular patient and/or target location. A series of arcs and straight tubes can be calculated that reach a particular target location. Target tube paths are generated from the resulting series of arcs and straight tubes. The path calculation may be weighted such that a change from one arc to another incurs an additional penalty. This causes a feasible pathway to occur, while reducing the total number of tubes and/or customized tubes required.

In an exemplary embodiment, custom shaping of nitinol tubes may be avoided by careful selection of a predefined set of tubes. In an exemplary system, tubes can be nested in either a set of fixed arcs, or in an alternating set of arc-straight-arc-straight tubes. Preparing appropriate predefined sets allows for simplified and speedy path calculations. Moreover, standard sets of cannulas can be produced in large quantities rather than requiring custom shaping and manufacturing. Having a pre-set pattern enables the potential reuse of the same Nested Cannula system extended to different lengths to reach different target locations in the same individual in the same procedure. Predetermined shape and extension distance patterns for a particular patient can significantly reduce costs associated with a particular medical procedure. Manual deployment provides the ability for a technician/clinician, such as a surgeon, to provide physical guidance and control over the insertion process aided by tactile, visual, location or other types of feedback. Particular steps can be taken to facilitate accurate manual deployment including but, not limited to:

(1) etching distance markings into the tubes so that a precision distance can be deployed at each motion;

(2) etching orientation markings into the tubes to enable the proper orientation of the tubes;

(3) in a particular situation where a fixed set of shapes are required and the cannula is not intended to be used for a different target location, the tubes can have an interlocking ridge to lock the proper orientation relative to each tube; and (4) tubes may be cut to the proper length so that each successive tube terminates at the same location as the larger (parent) tube.

The number of tubes associated with an exemplary Nested Cannula system is limited by the diameter of the outer most tube. Particular steps can be taken to facilitate minimizing the number of tubes used to reach a target location in a particular anatomical region including but not limited to:

(1) adding a handicap within the calculation methodology for each new arc type or orientation causes a feasible pathway to occur, while reducing the total number of tubes and/or customized tubes required; and (2) including a highly flexible catheter, guide wire, and/or fiber optics to the end of the last extending tube to reach the farthest most complicated target location.

Exemplary Nested Cannula systems and methods can be used for a variety of medical, diagnostic and/or surgical applications, including lung cancer diagnosis, biopsy, photodynamic treatment and the like. For example, a Nested Cannula system can be used to perform a biopsy using image guidance and tracking for precision delivery of biopsy tools. A Nested Cannula system according to the present disclosure facilitates autofluorescence by using image guidance, tracking and fiber optic transmission and sensing. Indeed, exemplary Nested Cannula systems and methods associated with the present disclosure can be utilized in lung cancer therapy for reaching target locations beyond current practice.

Exemplary Nested Cannula systems and methods according to the present disclosure may, in particular, be useful in PDT. PDT is already clinically approved and reimbursed for lung carcinoma. In an exemplary PDT procedure, an agent (e.g., Photofrin®) is injected 24-72 hours prior to therapy, accumulates at cancer sites, and is activated by light delivered within 1 cm of a lesion. Unfortunately, bronchoscopes only reach the largest passages, representing about 33% of the lung. The smaller passages, where oxygen exchange occurs, cannot be reached (or reached accurately) by current techniques, systems or methods. Lesions or tumors not surrounding passages or vessels may need to be treated from nearby vessels or passages. A Nested Cannula system according to the present disclosure allows for the determination of and reach to relatively difficult but effective target locations through the use of high-resolution images and tracking. In an exemplary embodiment, a Nested Cannula system according to the present disclosure may work in conjunction with current bronchoscope practice.

Exemplary Nested Cannula systems can be utilized for biopsy of hard to reach anatomical regions to determine the extent and/or need for molecular therapy or other intervention. It can also be utilized for 'on the spot' delivery of electronically generated radiation, e.g., using Xoft's Axxent miniaturized 2.25 mm X-ray source. In a cardiac environment, an exemplary Nested Cannula system associated with the present disclosure can be useful in accessing difficult locations or orientations. For vascular applications, a Nested Cannula system according to the present disclosure can reach through complex vessels currently unreachable by existing medical techniques. Moreover, the risk of dislodging clots is reduced since Nested Cannulas produce friction only for a portion of the entry path rather than the entire distal length.

The present disclosure provides for Nested Cannula systems that are also operable for minimally invasive surgeries for gallstones. The cannulas can be adapted to reach a gallbladder for removal. For gastroenterology, an exemplary Nested Cannula system according to the present disclosure is adapted to deliver PDT to a particular GI tract and reach target locations previously unreachable. It is also possible to reach target locations into a brain through minimally invasive vasculature. Although this example is given for 3D images, the solution works for 2D images as well, with 2D neighborhoods encapsulating the permitted motions of a device.

Figure 12:
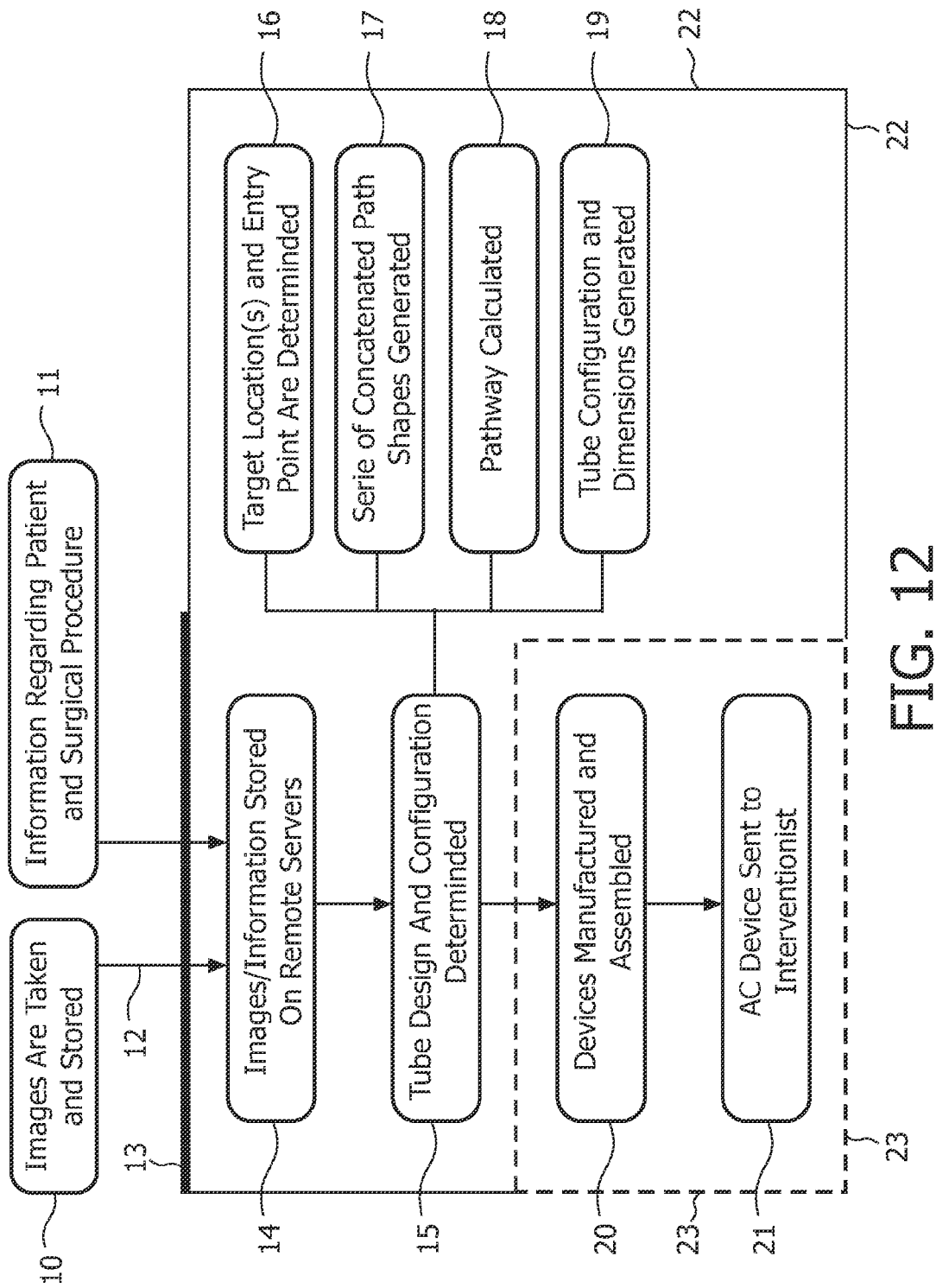
FIG. 12 illustrates the disclosed Nested Cannula configuration and design system and methods adapted to a web-based business platform.

The present disclosure also provides for a web-based business. As shown in FIG. 12, the Nested Cannula design and configuration system and methods work well in a web-based business platform. Digital 3D image(s) 10 are generated from one of a set or combination of imaging modality systems (CT, MRI, Ultrasound, Pet, fluoroscopy, etc.) of an anatomical region. The images can be readily sent directly by the imaging system, or via a PACS (picture archiving system) to a remote server 14 via the Internet 12 or other network. A radiologist, imaging technician or interventionalist can also transmit information regarding the patient, requirements of the surgical procedure being performed, and/or other pertinent information 11. For example, the 3D target location for a biopsy might be identified based on the expertise of the radiologist, or might be selected by a Computer Aided Detection (CAD) system. Depending upon the procedure, a preferred entry angle may also be provided. A webpage or other interface 13 facilitates the manual transfer of images and related information. From the transferred 3D images and data located on the server, the tube design and configuration is determined 15. The configuration and dimension information is then used to manufacture each tube of the Nested Cannula.

Preferably, the set of tubes is limited to the combination of a predetermined set of tubes having appropriate gap for acceptable friction as the tubes move within each other. The tubes are also preferably selected so that they are of increasing wall thickness. Therefore, a smaller diameter tube will also have a smaller wall thickness than a larger diameter tube. This reduces the affect of smaller tubes on a larger tube's shape.

The manufacture and assembly 20 of the tubes can be completed onsite 22 or remotely 23 by transmitting the configuration and dimensioning information to a remote facility or third party. Upon completion of manufacture and assembly, the Nested Cannula device is then sent directly to the interventionalist 21. The assembled Nested Cannula device can be delivered to the interventionalist within a day or two.

The present disclosure also provides for light-based detection of cancers. An additional feature of photosensitive drugs is that they exhibit fluorescence. When illuminated at typically a shorter wavelength, the compound will fluoresce. This fluorescence may be used to locate diseased tissue in a procedure sometimes called photodynamic diagnosis (PDD). This shorter wavelength light can be used to scan for potential cancers.

For the procedure, a photosensitive drug is administered to the patient. The drug may for example be the prodrug 5-ALA. 5-ALA is converted to PPIX, which is a photosensitive drug. After few hours the photosensitizer will accumulate at higher concentrations in the diseased tissue as compared to healthy tissue.

In the preferred embodiment, the light highlights the diseased tissue for treatment by photodynamic detection. That is, the Nested Cannula contains a light source and a detector to measure fluorescence of the tissue. A photosensitizer such as 5-ALA is converted to PPIX at the diseased tissue and the PPIX will fluoresce. The absorption peak for fluorescence is approximately 410 nm. Emission is in the red around 600-650 nm. The Nested Cannula thus contains a light source such as an LED emitting near 410 nm, which may also be delivered via fiber optics to direct light onto the tissue. The light reflected from the tissues is collected, optionally by fiber optic cable, and focused onto one or several photodetectors. The photodetectors are spectrally filtered to correspond to the fluorescence band, in this case around 600-650 nm. When the fluorescence signal exceeds a pre-set threshold then a tumor site has been successfully located.

Clearly, although this example is provided in 3D, a 2D plan and path can be generated by utilizing only one slice of the image. The only neighborhood entries that will be employed are those that lie on the plane, and the series of straight and arc tubes will stay on the plane.

Although the present disclosure has been described with reference to exemplary embodiments and implementations thereof, the disclosed systems and methods are not limited to such exemplary embodiments/implementations. Rather, as will be readily apparent to persons skilled in the art from the description provided herein, the disclosed systems and methods are susceptible to modifications, alterations and enhancements without departing from the spirit or scope of the present disclosure. Accordingly, the present disclosure expressly encompasses such modification, alterations and enhancements within the scope hereof.

What is claimed:

1. A Nested Cannula system comprising:
  a plurality of concentric telescoping tubes nested within each other configured and dimensioned to reach a target location by generating a tube pathway through a set of arcs determined from three dimensional image data of a particular anatomical region,
    wherein each arc is determined between an origin and the target location,
    wherein each arc has a curvature independent of the target location, and
    wherein said target location is determined by the requirements of (i) a medical procedure and (ii) the location and orientation of an anatomical structure.

2. The system of claim 1, wherein the target location within the three dimensional image data of the anatomical region is defined using six parameters.

3. The system of claim 1, wherein the surgical procedure is photodynamic therapy.

4. The system of claim 1, wherein the tubes are configured and dimensioned to reach relatively small or complex target locations within the anatomical region.

5. The system of claim 1, wherein the three dimensional image data is generated by an imaging system such as a CT scanner, fluoroscopy system, x-ray system, ultrasound system or MRI system.

6. The system of claim 1, wherein the image data of the anatomical region is used to configure and dimension each of the plurality of tubes to define a particular shape and extension length of each of the plurality of tubes.

7. The system of claim 6, wherein the defined shape and extension length of each of the plurality of tubes allows for determining whether a target location is reachable.

8. The system of claim 1, wherein the plurality of tubes are configured and dimensioned to pre-set shapes and extension lengths for a particular anatomical region.

9. The system of claim 8, wherein the pre-set plurality of tubes include alternating curved and straight tubes.

10. The system of claim 1, wherein the plurality of tubes are configured and dimensioned to pre-set shapes and extension lengths for a particular anatomical region associated with a particular individual.

11. The system of claim 1, wherein the tubes are configured and dimensioned using inverse kinematics.

12. The system of claim 1, wherein the anatomical region is a lung.

13. The system of claim 1, wherein the anatomical structure is cancerous.

14. The system of claim 1, wherein the tubes are adapted to prevent tissue damage resulting from insertion friction by creating a barrier with the outer most tube of the plurality of tubes.

15. The system of claim 1, wherein the tubes include a medical device member at the tip of the furthest extending tube adapted to perform the medical procedure at a particular target location.

16. The system of claim 15, wherein the medical device member is selected from the group consisting of: a catheter, a telescopic tip, a guide wire, an ablation device, a cautery device, a suture device, an electro-stimulation device, a lavage mechanism, an angioplasty balloon, a thermoplasty device and a fiber optic device.

17. The system of claim 1, wherein the tubes includes a medical device member at the tip of the furthest extending tube is able to perform photodynamic therapy at a particular target location.

18. The system of claim 1, further comprising a driver mechanism adapted to guide the plurality of tubes to a target location.

19. The system of claim 1, wherein the tubes are adapted to allow manual guidance and control over the insertion of the tubes into the anatomical region aided by a tactile feedback.

20. The system of claim 1, wherein one or more of the tubes is fabricated from nitinol or from a biocompatible plastic.

21. The system of claim 1, wherein a point on the tube pathway is a start or goal and is selected based on where the relative free space is smaller or more constrained within the particular region.

22. A method for Nested Cannula configuration comprising the steps of:
(a) acquiring image data of an anatomical region, in three or more dimensions;
(b) determining a target location in the anatomical region;
(c) generating a series of concatenated path shapes between an origin and the target location to form a pathway, wherein each path shape has a curvature independent of the target loaction; and (d) generating a plurality of concentric telescoping tubes nested within each other configured and dimensioned to reach the target location using the concatenated path shapes.

23. The method of claim 22, wherein the image data is generated from an imaging system such as a CT scanner, fluoroscopy system, ultrasound system or MRI system.

24. The method of claim 22, wherein the anatomical region is a lung.

25. The method of claim 22, further comprising identifying anatomical structure from the data, wherein the anatomical structure is cancerous.

26. The method of claim 22 wherein the tubes include a medical device member at the tip of the farthest extending tube, the medical device member being adapted to perform a medical procedure at a particular target location.

27. The method of claim 26, wherein the medical device member is selected from the group consisting of: a catheter, a telescopic tip, a guide wire, an ablation device, a cautery device, a suture device, an electro-stimulation device, a lavage mechanism, an angioplasty device, a thermoplasty device and a fiber optic device.

28. The method of claim 22, wherein the target location is determined by the requirements of a medical procedure and the location and orientation in of an identified anatomical structure.

29. The method of claim 22, wherein the target location is determined in regards to photodynamic therapy and the location and orientation of an identified anatomical structure.

30. The method of claim 22, wherein the plurality of tubes alternate between straight tubes and curved tubes.

31. The method of claim 22, wherein the tubes are configured or dimensioned using inverse kinematics.

32. The method of claim 22, wherein one or more of the tubes is fabricated from Nitinol 33. The method of claim 22, wherein the target location is defined by three parameters, and an approach angle is determined from reachable neighboring states.

34. The method of claim 22, wherein the step of generating a series of concatenated path shapes also generates tube diameters that will fit within the allowed space, avoiding obstacles.

35. A Nested Cannula design and configuration business system comprising:
(a) receiving through a web-based interface, image data of an anatomical region and structure;
(b) receiving information regarding a particular medical procedure or patient;
(c) determining a target location by the requirements of a medical procedure and a location and orientation of an anatomical structure in the anatomical region;
(d) generating a series of concatenated path shapes between an origin and target location within the anatomical region to form a pathway, wherein each path shape has a curvature independent of the target location; and
(e) generating a specification for a plurality of concentric telescoping tubes nested within each other configured and dimensioned to reach the target location using the concatenated path shapes.

36. The system of claim 35, wherein the anatomical structure is a lung.

37. The system of claim 35, wherein the information is related to a medical procedure and the medical procedure is photodynamic therapy.

38. The system of claim 35, further comprising the step of manufacturing or assembling the concentric telescoping tubes.

* * * * *